（12）United States Patent
Dömling et al.

(10) Patent No.: US 7,776,814 B2
(45) Date of Patent: *Aug. 17, 2010

(54) TUBULYSIN CONJUGATES

(75) Inventors: Alexander Dömling, Munich (DE); Lutz Weber, Germering (DE)

(73) Assignee: R&D-Biopharmaceuticals GmbH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/520,791

(22) PCT Filed: Jul. 9, 2003

(86) PCT No.: PCT/EP03/07415

§ 371 (c)(1),
(2), (4) Date: Jan. 8, 2005

(87) PCT Pub. No.: WO2004/005326

PCT Pub. Date: Jan. 15, 2004

(65) Prior Publication Data

US 2005/0249740 A1 Nov. 10, 2005

(30) Foreign Application Priority Data

Jul. 9, 2002 (DE) ................ 102 30 875
Feb. 11, 2003 (DE) ................ 103 05 531

(51) Int. Cl.
*A61K 38/00* (2006.01)
*A61K 39/395* (2006.01)
*A61K 31/7056* (2006.01)

(52) U.S. Cl. .............. 514/2; 514/92; 530/332
(58) Field of Classification Search ............ None
See application file for complete search history.

(56) References Cited

U.S. PATENT DOCUMENTS

2002/0169125 A1 * 11/2002 Leung et al. .......... 514/12

FOREIGN PATENT DOCUMENTS

DE  19638870 A1 *  3/1998
DE  1008089 A1 * 10/2001

OTHER PUBLICATIONS

Sasse, et al., The Journal of Antibiotics, 2000, 53, 879-885.*
Greenwald, Journal of Controlled Release, 2001, 74, 159-171.*
Greenwald, 2001, Journal of Controlled Release, 74, 159-171.*
Duncan, 2001, Journal of Controlled Release, 74, 135-146.*
Sasse, F. et al. "Tubulysins, new cytostatic peptides from myxobacteria acting on microtubuli production, isolation, physicochemical and biological properties" *Journal of Antibiotics*, Japan Antibiotics Research Association, Bd. 53, Nr. 9, Sep. 2000, Seiten 879-885, XP009014740.
Greenwald, R.B. "PEG drugs: an overview" *Journal of Controlled Release*, Elsevier Science Publishers B.V. Amsterdam, NL, Bd. 74, Nr.1-3, Jul. 6, 2001, Seiten 159-171, XP004297521.
Duncan R. et al. "Polymer-drug conjugates, PDEPT and PELT: basic principles for design and transfer from the laboratory to clinic" *Journal of Controlled Release*, Elsevier Science Publishers B.V. Amsterdam, NL, Bd. 74, NR. 1-3, Jul. 6, 2001, Seiten 135-146, XP004297519.
Garnett, M. C. "Targeted drug conjugates: Principles and progress" *Advanced Drug Delivery Reviews*, Bd. 53, Nr. 2, Dec. 17, 2001, Seiten 171-216, XP002261805.

* cited by examiner

*Primary Examiner*—Andrew B Kosar
*Assistant Examiner*—Satyanarayana R Gudibande
(74) *Attorney, Agent, or Firm*—Edwards Angell Palmer & Dodge LLP; Peter F. Corless; Nicholas J. DiCeglio, Jr.

(57) ABSTRACT

The invention relates to novel tubulysin conjugates (e.g. of tubulysin A) and the use thereof in the treatment of cancer diseases.

19 Claims, No Drawings

TUBULYSIN CONJUGATES

CROSS REFERENCE TO RELATED APPLICATIONS

This application is a U.S. National Stage application under 35 U.S.C. §371 of International Application No. PCT/EP03/07415, filed Jul. 9, 2003 which claims the benefit of German Application No. 103 05 531.2, filed Feb. 11, 2003 and German Application No 102 30 875.6, filed Jul. 9, 2002, each of which is incorporated by reference herein in its entirety.

BACKGROUND OF THE INVENTION

The present invention relates to novel tubulysin conjugates and the use thereof in the treatment of cancer diseases.

The tubulysins were for the first time isolated by the group of Höfle and Reichenbach (GBF Braunschweig) from a culture broth of strains of the Myxobacteria Archangium gephyra (F. Sasse et al. J. Antibiot. 2000, 53, 879-885; WO9813375; DE 10008089). These compounds show an extremely high cytotoxic activity against mammalian cell lines with IC50 values in the picomolar range and therefore, are of high interest as potential therapeutics against cancer.

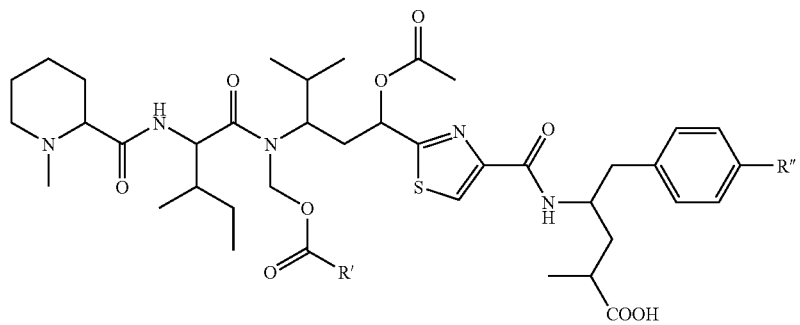

Tubulysin A: R' = CH$_2$CH(CH$_3$)$_2$;   R'' = OH
Tubulysin B: R' = CH$_2$CH$_2$CH$_3$;   R'' = OH
Tubulysin C: R' = CH$_2$CH$_3$;   R'' = OH
Tubulysin D: R' = CH$_2$CH(CH$_3$)$_2$;   R'' = H
Tubulysin E: R' = CH$_2$CH$_2$CH$_3$;   R'' = H
Tubulysin F: R' = CH$_2$CH$_3$;   R'' = H The extremely high cytotoxicity of some tubulysins also exhibits disadvantages: a high general toxicity as well as a low selectivity against normal cells.

The object of the present invention is to lower the toxicity of the tubulysins and to enhance their selectivity.

SUMMARY OF THE INVENTION

The present invention provides tubulysin conjugates of the general formula U—V—W, wherein U represents the Formula (I),

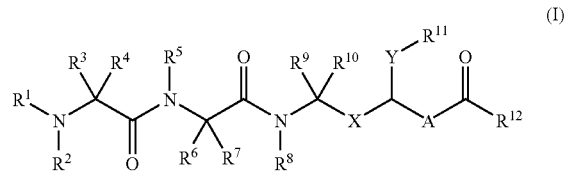

wherein

A is a optionally substituted five or six membered heteroaromatic system;

X is an oxygen atom, a sulfur atom, a group of the formula NR13 or CR14R15;

Y is an oxygen atom, a sulfur atom or a group of the formula NR16 and the terms $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ independently from each other a hydrogen atom, a alkyl-, alkenyl-, alkynyl-, heteroalkyl-, aryl-, arylalkyl-, heteroaryl-, heteroarylalkyl-, cycloalkyl-, heterocycloalkyl-, alkylcycloalkyl- or heteroalkylcycloalkyl-group or two of the groups together are part of a cycloalkyl- or heterocycloalkyl ring system, V is a linker and W is a polymer or a biomolecule.

In the present invention it was found that polymer conjugates and bioconjugates, resp., of special tubulysins exhibit a higher selectivity by a given cyctotoxicity as well as lower toxicity as the unconjugated compounds. The result is that predominantly cancer cells are targeted in the human and the animal body and healthy tissue is not affected.

DETAILED DESCRIPTION OF THE INVENTION

The term alkyl refers to a saturated straight or branched chain alkyl group, containing from one to twenty carbon atoms, preferably from one to twelve carbon atoms, especially preferred from one to six carbon atoms, for example methyl, ethyl, propyl, iso-propyl, iso-butyl, tert.-butyl, n-hexyl, 2,2-dimethylbutyl or n-octyl groups.

The terms alkenyl and alkinyl refer to at least partly unsaturated straight or branched chain alkyl groups, containing from two to twenty carbon atoms, preferably from two to twelve carbon atoms, especially preferred from two to six carbon atoms, for example ethenyl, propenyl, iso-propenyl, isoprenyl or hexa-2-enyl. Preferably exhibit alkenyl groups one or two (especially preferred one) double bonds resp. alkynyl groups one or two (especially preferred one) triple bonds.

The terms alkyl, alkenyl and alkynyl moreover refer to groups, wherein one or more hydrogen atoms are replaced by halogen atoms (preferably fluorine or chlorine) such as, for example the 2,2,2-trichloroethyl or the trifluoromethyl groups The term heteroalkyl refers to an alkyl, a alkenyl, or a alkynyl group as defined herein where one or more (preferably 1, 2 or 3) carbon atoms are replaced by an oxygen, nitrogen, phosphorous, boron, selenium, silicium or sulphur atom (preferably oxygen, sulfur or nitrogen). The term heteroalkyl furthermore refers to a caboxylic acid or a group derived from a carboxylic acid such as for example acyl (alkyl-CO—), acylalky, alkoxycarbonyl, acyloxy, acyloxyalkyl, carboxyalkylamide or alkoxycarbonyloxy.

Examples for heteroalky groups are groups of the formulas $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^{a-N(Rb)}$—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$, $R^a$—N($R^b$)—CS—S—$Y^a$—, $R_a$—S—CS—S—$Y^a$, $R^a$—O—CS—S—$Y^a$—, wherein $R^a$ is a hydrogen atom, a $C_1$-$C_6$-alkyl-, a $C_2$-$C_6$-alkenyl or a $C_2$-$C_6$-alkynyl group; $R^b$ is a hydrogen atom, a $C_1$-$C_6$-alkyl-, a $C_2$-$C_6$-alkenyl or a $C_2$-$C_6$-alkynyl group; $R^c$ is a hydrogen atom, a $C_1$-$C_6$-alkyl-, a $C_2$-$C_6$-alkenyl or a $C_2$-$C_6$-alkynyl group; $R^d$ is a hydrogen atom, a $C_1$-$C_6$-alkyl-, a $C_2$-$C_6$-alkenyl or a $C_2$-$C_6$-alkynyl group and $Y^a$ is a direct bond, a $C_1$-$C_6$-alkylene-, a $C_2$-$C_6$-alkenylene or a $C_2$-$C_6$-alkynylene group, wherein each heteroalkyl group contains at least one carbon atom and one or more hydrogen atoms can be replaced by fluoro or chloro atoms. Concrete examples for heteroalky groups are methoxy, trifluoromethoxy, ethoxy, n-propyloxy, iso-propyloxy, tert.-butyloxy, methoxymethyl, ethoxymethyl, methoxyethyl, methylamino, ethylamino, dimethylamino, diethylamino, iso-propylethylamino, methylaminomethyl, ethylaminomethyl, di-iso-propylaminoethyl, enolether, dimethylaminomethyl, dimethylaminoethyl, acetyl, propionyl, butyryloxy, acetyloxy, methoxycarbonyl, ethoxycarbonyl, N-ethyl-N-methylcarbamoyl or N-methylcarbamoyl.

Further examples for heteroalky groups are nitrile, isonitrile, cyanate, thiocyanate, isocyanate, isothiocyanate and alkylnitrile groups.

The term cycloalky refers to a saturated or partially unsaturated (e.g. cycloalkenyl) cyclic group which comprises of one or several rings (perferably 1 or 2) which contain in total three to fourteen ring carbon atoms, preferably three to ten (especially 3, 4, 5, 6 or 7) ring carbon atoms. The term cycloalkyl refers also to such groups in which one or more hydrogen atoms are replaced by fluoro, chloro, bromo or iodo atoms or OH, =O, SH, =S, $NH_2$, =NH, or $NO_2$ groups, e.g. cyclic ketones such as e.g. cyclohexanone, 2-cyclohexenone or cyclopentanone. Additional concrete examples for cycloalkyl groups are the cyclopropyl, cyclobutyl, cyclopentyl, spiro[4,5]decanyl, norbornyl, cyclohexyl, cyclopentenyl, cycloheadienyl, decalinyl, cubanyl, bicyclo[4.3.0]nonyl, tetralin, cyclopentylcyclohexyl, fluorocyclohexyl or the cyclohex-2-enyl group.

The term heterocycloalkyl refers to a cycloalkyl group as difined above in which one or more (preferably 1, 2 or 3) ring carbon atoms are replaced by an oxygen, nitrogen, silicon, selenium, phosphorous or sulfur atom (preferably oxygen, sulfur or nitrogen). Preferably the heterocycloalky group contains 1 or 2 rings with 3 to 10 (especially 3, 4, 5, 6 or 7) ring atoms. The term heterocycloalkyl refers also to such groups in which one or more hydrogen atoms are replaced by fluoro, chloro, bromo or iodo atoms or OH, =O, SH, =S, $NH_2$, =NH, or $NO_2$ groups. Examples thereof are the piperidyl, morpholinyl, urotropinyl, pyrrolidinyl, tetrahydrothiophenyl, tetrahydropyranyl, tetrahydrofuryl, oxacyclopropyl, azacyclopropyl or 2-pyrazolinyl group as well as lactams, lactones, cyclic imides and cyclic anhydrides.

The term alkylcycloalkyl refers to groups which according to the definitions given above contain either cycloalkyl and alky, alkenyl or alkynyl groups, e.g. alkylcycloalkyl, alkylcycloalkenyl, alkenylcycloalkyl and alkynylcycloalkyl groups. Preferably a alkylcyckloalkyl group contains a cycloalkyl group which has one or two ring systems which in total comprises 3 to 10 (especially 3, 4, 5, 6 or 7) carbon atoms and one or two alkyl, alkenyl or alkynyl groups with 1 or 3 to 6 carbon atoms.

The term heteroalkylcycloalkyl refers to alkylcycloalkyl groups in which according to the definitions given above one or more (preferably 1, 2 or 3) carbon atoms are replaced by an oxygen, nitrogen, silicon, selenium, phosphorous or sulfur atom (preferably oxygen, sulfur or nitrogen). Preferably the heteroalkylcycloalky group contains 1 or 2 ring systems with 3 to 10 (especially 3, 4, 5, 6 or 7) ring atoms and one or two alkyl, alkenyl, alkynyl or heteroalkyl groups with 1 or 2 to 6 carbon atoms. Examples of such groups are alkylheterocycloalkyl, alkylheterocycloalkenl, alkenylheterocycloalkyl, akynylheterocycloalkyl, heteroalkylcycloalkyl, heteroalkylheterocycloalkyl and heteroalkylheteocycloalkenyl in which the cyclic groups are saturated or single, double or triple unsaturated.

The term aryl and Ar, resp., refer to a aromatic group which has one or more rings which in total contain 6 to 14 ring carbon atoms, preferably 6 to 10 (especially 6) ring carbon atoms. The term aryl (resp. Ar) refer further to such groups in which one or more hydrogen atoms are replaced by fluoro, chloro, bromo or iodo atoms or OH, SH, $NH_2$ or $NO_2$ groups. Examples are the phenyl, naphthyl, 2-fluorophenyl, anilinyl, 3-nitrophenyl or 4-hydroxyphenyl group.

The term heteroaryl refers to a aromatic group which has one or more rings which in total comprise 5 to 14 ring atoms, preferably 5 to 10 (especially 5 or 6) ring atoms and one or more (preferably 1, 2, 3 or 4) oxygen, nitrogen, phosphorous or sulfur ring atoms (preferably O, S or N). The term heteroaryl refers further on such groups in which one or more hydrogen atoms are replaced by fluoro, chloro, bromo or iodo atoms or OH, SH, $NH_2$ or $NO_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, chinolinyl, purinyl, carbazolyl, acridinyl, pyrimidyl, 2,3'-bifuryl, 3-pyrazolyl and isochinolinyl groups.

The term aralkyl refers to groups which according to the above definitions contain either aryl and alkyl, alkenyl, alkynyl and/or cycloalkyl groups such as e.g. arylalkyl, arylalkenyl, arylalkynyl, arylcycloalkyl, arylcycloalkenyl, alkylarylcycloalkyl and alkylarylcycloalkenyl groups. Concrete examples for aralkyls are toluene, xylene, mesitylene, styrole, benzylchloride, o-fluorotoluene, 1H-indene, tetraline, dihydronaphthaiine, indanone, phenylcyclopentyl, cumol, cyclohexylphenyl, fluorene and indan. Preferably a aralkyl group contains one or two ring systems (1 or 2 rings) with in total 6 to 10 ring carbon atoms and one or two alkyl, alkenyl and/or alkynyl groups with 1 or 2 to 6 carbon atoms and/or a cycloalkyl group with 5 or 6 ring carbon atoms.

The term heteroaralkyl refers to a aralkyl group as defined above in which one or more (preferably 1, 2, 3 or 4) carbon atoms are replaced by oxygen, nitrogen, silicon, selenium, phosphorous, boron or sulfur atom (preferably oxygen, sulfur or nitrogen), i.e. to groups which according to the definitions above contain either aryl or heteroaryl resp., and alkyl, alkenyl, alkynyl and/or heteroalkyl and/or cycloalkyl and/or heterocycloalkyl groups. Preferably a heteroaralkyl group contains one or two aromatic ring systems (1 or 2 rings) with in total 5 or 6 to 10 ring carbon atoms and one or two alkyl, alkenyl and/or alkynyl groups with 1 or 2 to 6 carbon atoms and/or a cycloalkyl group with 5 or 6 ring carbon atoms whereby 1, 2, 3 or 4 of these carbon atoms are replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteoarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, whereby the cyclic groups are saturated or single, double or triple unsaturated. Concrete examples are the tetrahydroisochinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The terms cycloalkyl, heterocycloalkyl, alkylcycloalkyl, heteroalkylcycloalkyl, aryl, heteroaryl, aralkyl and heteroaralkyl refer also to groups in which one or more hydrogen atoms of such groups are replaced by fluoro, chloro, bromo or iodo atoms or OH, $=$O, SH, $=$S, $NH_2$, $=$NH, or $NO_2$ groups.

The term "optionally substituted" refer to groups in which one or more hydrogen atoms are replaced by fluoro, chloro, bromo or iodo atoms or OH, $=$O, SH, $=$S, $NH_2$, $=$NH, or $NO_2$ groups. This term also refer to groups which are exclusively or additionally substituted with unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_7$-$C_{12}$ aralkyl or $C_2$-$C_{11}$ heteroalkyl groups.

The term linker refers to a group which is used to connect compounds of the formula (I) with a polymer or a biomolecule. A linker can be a direct bond, a alkylene, alkenylen, alkynylene heteroalkylene, arylene, heteroarylene, cycloalkylene, alkylcycloalkylene, heteroalkylcycloalkylene, heterocycloalkylene, aralkylene or a heteroaralkylene. Preferred are linkers which are stable towards blood plasma (especially stable towards hydrolysis), metabolically cleavable and after the cleavage non-toxic.

Examples for linkers are described in P. Seneci, Solid-Phase Synthesis and Combinatorial Technologies, John Wiley & Sons, New York 2000; D. Obrecht and J. M. Villalgordo, Solid-Supported Combinatorial and Parallel Synthesis of Small-Molecular-Weight Compound Libraries, Tetrahedron Organic Chemistry Series Volume 17, Elsevier Science Ltd., Oxford, 1998 as well as in F. Z. Dörwald, Organic Synthesis on Solid Phase, Wiley-VCH, Weinheim, 2000, those examples are included under reference. As examples are named here the trityl linker, the Wang linker, the SAS-RIN™-linker, the Rink acid linker, the benzhydrylalkohol linker, the HMBA-linker as well as polymeric benzylhalogenid (linker of the Merrifield resin) and the PAM-linker.

As polymers especially synthetic polymers come into question such as e.g. polyethylenglycol (MW=200, 300, 400, 30,000, 35,000, 40,000; especially MW=25,000-100,000 Da, perferably 25,000-50,000 Da), polyethylenglycol dendrimers, polyacrylic acid, hydroxyethyl starch (HES), polylacticglycolid, poly-D,L-lactic acid-p-dioxanonepolyethylene glycol block copolymer (PLA-DX-PEG), poly(ortho) ester, polyglutamate, polyaspartate, polymer from α-β-unsaturated monomers: (meth)acrylic acid, crotonic acid, maleic acid, maleic anhydride, fumaric acid, itaconic acid/anhydride, etc. Comonomers including: vinyl ether, vinyl ester, vinyl amide, olefins, diallyl-dialkyl-ammonium-halogenes, prefered vinyl ether, poly-(diethylene glycol adipat), poly ethylene imine, poly glycolide, poly urea, poly limonene (=polylimo), poly (2-methyl-1,3-propylene adipat), grafted polymers, graft (block-) polymers with othe polymers.

As biomolecules e.g. glycoproteins, lipoproteins, lectins, hormones e.g. somatostatin and somatostatin analogues, resp., synthetic hormon analogues, albumine, liposomes, DNA, dextrane, biotin, streptavidine, avidine, cells or antibodies come into question. Preferably the biomolecule is an antibody, more preferred a monoclonal antibody (e.g. herceptine).

Further examples for linkers, polymers and biomolecules are described in G. T. Hermanson, Biokonjugate Techniques, Academic Press, San Diego, 1996, whose examples therein are included under reference.

It should be appreciated that compounds of the formula (I) because of their substitution may contain one or more chirality centers. Therefore, the present invention relates either all possible pure enantiomers and all possible pure diastereoisomers as well as their mixtures in every mixing ratio.

Preferred X is a $CH_2$ group.

Moreover preferred Y is an oxygen atom.

Further preferred A has the following structure:

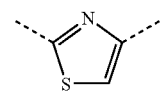

Furthermore preferred $R^1$ and $R^3$ are together part of a cycloalkyl ring; more preferred $R^1$ and $R^3$ together are of the formula —$(CH_2)_4$—.

Further preferred $R^2$ is a $C_1$-$C_4$ alkyl group, more preferred a methyl group.

Furthermore preferred $R^4$, $R^5$, $R^6$ and $R^{10}$ are hydrogen atoms.

Moreover preferred $R^7$ is a alkyl group; more preferred a group of the formula —$CH(CH_3)CH_2CH_3$.

Furthermore preferred $R^8$ is a hydrogen atom, a alkyl, alkenyl or a heteroalkyl group; more preferred a group of the formula —$CH_2C(=O)R^{17}$, whereby $R^{17}$ is a $C_1$-$C_6$ alkyl or a $C_2$-$C_6$ alkenyl group.

Moreover preferred $R^9$ is a alkyl group; more preferred a group of the formula —$CH(CH_3)_2$.

Further preferred $R^{11}$ is a hydrogen group or a acetyl group.

Further preferred $R^{12}$ is a group of the formula $NHR^{18}$ whereby $R^{18}$ is a heteroalkyl group.

More preferred $R^{18}$ has the following structures:

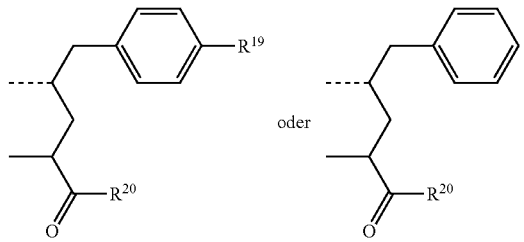

wherein $R^{19}$ and $R^{20}$ independentely from each other are hydrogen atoms, OH, $NH_2$, alkoxy, alkenyloxy, alkynyloxy, heteroalkyl, aryloxy, heteroaryloxy, cycloalkyloxy, alkylcycloalkyloxy, heteroalkylcycloalkyl, heterocycloalkyloxy, aralkyloxy or heteroaralkyl groups; more preferred $R^{19}$ and $R^{20}$ are hydroxy groups. In case the phenyl ring of both of these structures can be substituted (e.g. by a $NO_2$ group).

More preferred the compound of formula (I) is Tubulysin A.

Further preferred is the linker connected to compounds of the formula (I) via the residues $R^8$, $R^{11}$, $R^{19}$ or $R^{20}$; more preferred via the residues $R^{19}$ or $R^{20}$.

Further preferred the polymer is a polyethyleneglycol PEG (especially a PEG with a molecular weight of more than 30 kDa to 100 kDa, preferred of max. 50 kDa), which especially is bound to Tubulysin A via $R^{20}$ (in case with a linker V).

More preferred the conjugates (U—V—W) in the present invention comprise the following formula wherein the stereochemistry corresponds to the one of the natural Tubulysin A:

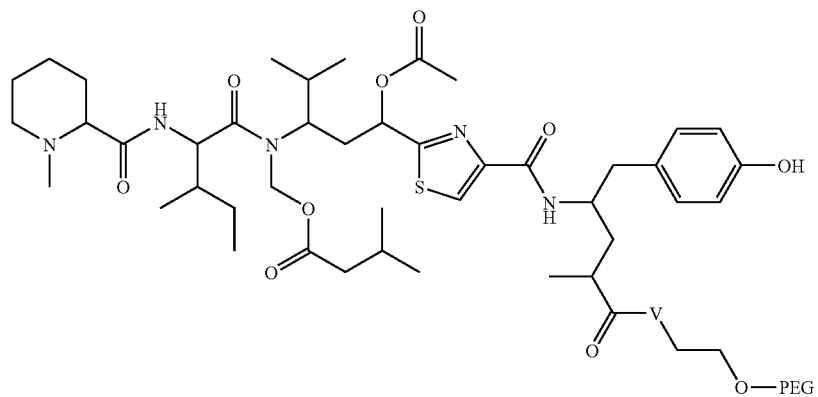

Preferred V is an oxygen atom, a NH group or a group of the formula —O—$(CR^aR^b)_n$—O— (whereby $R^a$ and $R^b$ are independently from each other $C_1$-$C_6$ alkyl groups or together part of cycloalkyl group and n is 1 or 2), —NH—$R^c$—NH—CO—$CH_2$—O—, —O—$R^c$—O—CO—$CH_2$—O— or a group of the formula —O—$R^c$—O— (whereby $R^c$ is a alkylene, arylene or a cycloalkylene group).

Pharmacologically acceptable salts, solvates, hydrates or formulations of the herein described conjugates are also part of the present invention. Examples for pharmacologically acceptable salts of compounds of the formula (I) are salts of physiologically acceptable mineralic acids such as hydrochloric acid, sulfuruc acid and phosphoric acid or salts of organic acids such as methansulfonic acid, p-toluenesulfonic acid, lactic acid, acetic acid, formic acid, trifluoroacetic acid, citric acid, succinic acid, fumaric acid, maleinic acid and salicylic acid. Compounds of the formula (I) can be solvated, especially hydrated. The hydratisation can occur e.g. during the preparation process or as consequence of the hygroscopic nature of the initially water free compounds of the formula (I).

The pharmaceutical compositions in the present invention contain at least one compound of the formula (I) as active ingredient and optionally carriers and/or adjuvants.

The therapeutic use of compounds of the formula (I), their pharmacologically acceptable salts and solvates, resp. and hydrates as well as formulations and pharmaceutical compositions is also part of the present invention.

The use of these active ingredients for the manufacturing of drugs is also part of the present invention. Furthermore, the present compounds are of great interest for the prevention and/or treatment of fungal infections (i.e. as antifungal agents), rheumatoid arthritis, inflammatory diseases, immunologically caused diseases (e.g. diabetes type 1), autoimmuno diseases as well as tumor diseases. In general compounds of the formula (I) will be administered by using the known and acceptable modes known in the art, either alone or in combination with any other therapeutic agent. Such therapeutically useful agents can be administered preferably parenteral, e.g. as injectable solution. For the production of liquid solutions one may use excipients as are e.g. water, alcohols or aqueous saline. The pharmaceutically useful agents may also contain additives for conservation, stabilisation, salts to change the osmotic pressure, buffers and antioxidants.

Combinations with other therapeutic agents may contain further active ingredients which are usually employed in the therapy of tumor diseases.

EXAMPLES

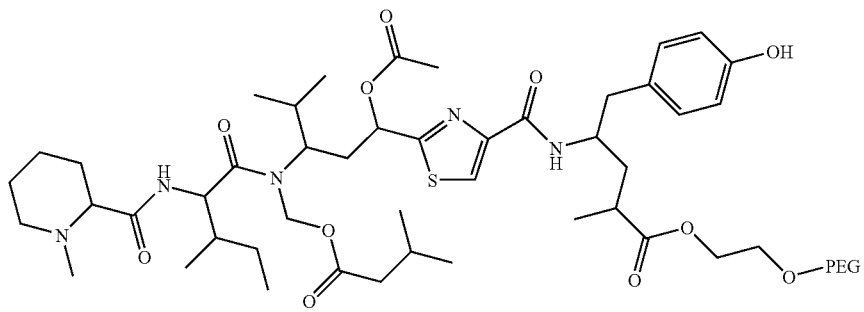

To a solution of 0.056 mmol Tubulysin A and 0.125 mmol PEG (6 kDa, 10 kDa, 20 kDa, 35 kDa and 40 kDa, resp.) in a mixture of 3 ml acetonitrile and 1 ml of DMF was added at 0° C. 0.1 mmol 2-chloro-1-methylpyridinium iodide (Mukaiyama reagent) and 0.2 mmol 4-dimethyl aminopyridine (DMAP). The reaction mixture was stirred for 2 h at 0° C. and another 60 h at room temperature. Then the mixture was evaporated, dissolved in 15 ml of dichloromethane and washed with each 5 ml water, NaHCO₃ (aq), water and saturated sodium chloride solution. The organic phase was dried over Na₂SO₄ and the solvent was removed under reduced pressure. The residue was dissolved in 8 ml dichloromethane and under stirring dry ether was added until the solution became turbid and was allowed to stand for one hour. The solid was collected by filtration and washed with ether. The desired products were obtained as white powders.

The PEG dicarbonic acids (6 kDa, 10 kDa, 20 kDa, 35 kDa bzw. 40 kDa) as well as their conjugation with Tubulysin A were prepared in accordance to the procedure described in R. B. Greenwald et al. J. Med, Chem. 1996, 39, 424-431.

The invention claimed is:
1. A compound in the general formula U—V—W, wherein U refers to the Formula (I),

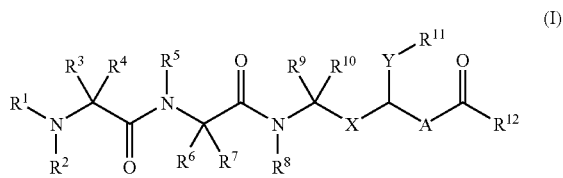

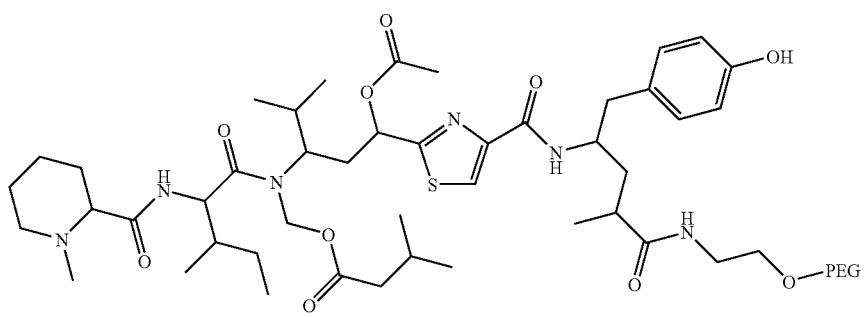

The diamines of the polyethyleneglycols (6 kDa, 10 kDa, 20 kDa, 35 kDa bzw. 40 kDa) as well as their conjunction with Tubulysin A were prepared in accordance to the procedure described in R. B. Greenwald et al. Bioorg. Med. Chem. 1998, 6, 551-562.

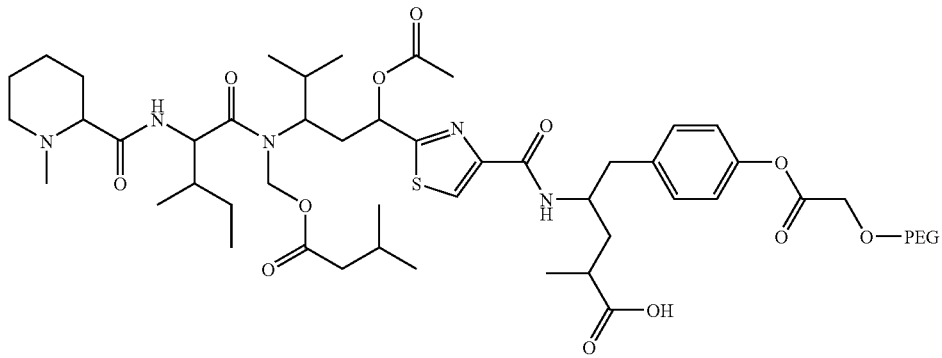

wherein
A has the following structure

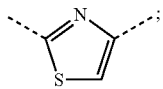

X is $CH_2$;

Y is an oxygen atom;

$R^1$ and $R^3$ together are of the formula —$(CH_2)_4$—;

$R^2$ is a $C_1$-$C_4$ alkyl group;

$R^4$, $R^5$, $R^6$, and $R^{19}$ are hydrogen atoms;

$R^7$ is an alkyl group;

$R^8$ is a hydrogen atom, an alkyl, alkenyl, or a heteroalkyl group $R^9$ is an alkyl group;

$R^{11}$ is an acetyl group;

$R^{12}$ is a group of formula $NHR^{18}$;

$R^{18}$ has the following structures:

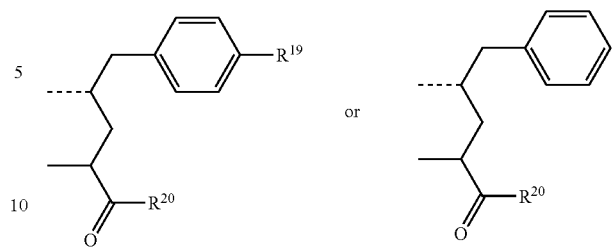

wherein $R^{19}$ is H or OH and $R^{20}$ is —V—W or wherein $R^{19}$ is —V—W and $R^{20}$ is OH, $NH_2$, or a heteroalkyl group;

V is an oxygen atom, a NH group, or a heteroalkylene group wherein the heteroatoms are selected from O, S, and N; and W is polyethylene glycol (PEG) or a cyclodextrin comprising polyethylene glycol (PEG).

2. A method for treating a patient suffering from breast cancer, cervical cancer, ovarian cancer, colorectal cancer or non-small cell lung cancer, comprising administering to the patient one or more compounds of claim 1.

3. A compound of claim 1 having the following formula:

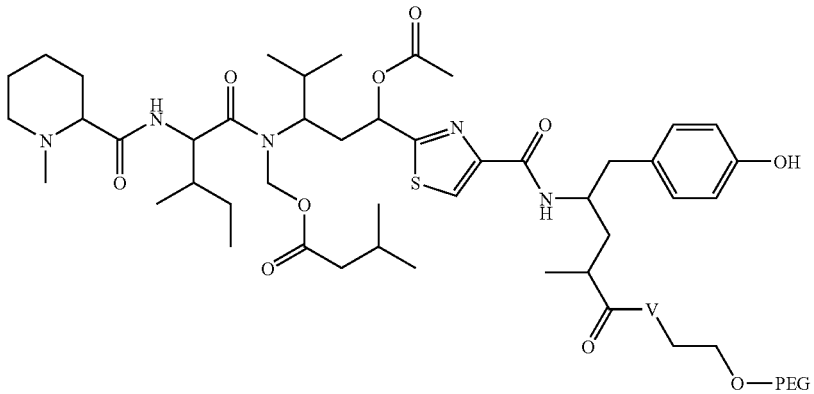

wherein V is an oxygen atom; a NH group; a group of the formula —O—$(CR^aR^b)_n$—O— where $R^a$ and $R^b$ are independently $C_1$-$C_6$alkyl groups or together part of cycloalkyl group and n is 1 or 2; —NH—$R^c$—NH—CO—$CH_2$—O—; —O—$R^c$—O—$CH_2$—O—; or a group of the formula —O—$R^c$—O— where $R^c$ is alkylene, arylene or a cycloalkylene group.

4. The compound of claim 3 wherein V is oxygen.

5. The method of claim 2 wherein a compound having the following formula is administered:

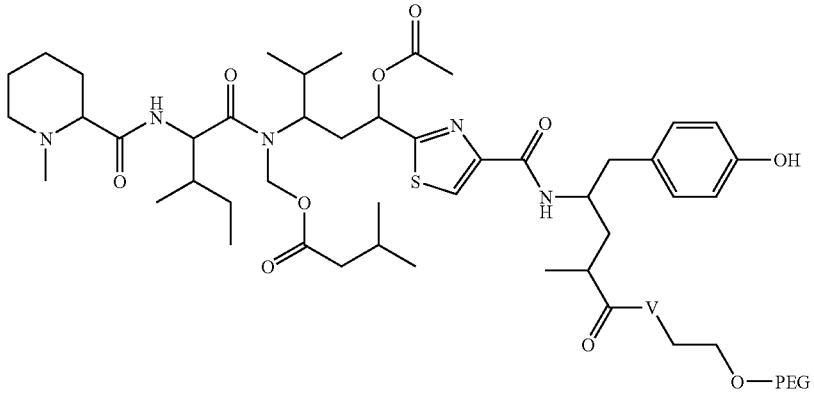

wherein V is an oxygen atom; a NH group; a group of the formula —O—(CR$^a$R$^b$)$_n$—O— where R$^a$ and R$^b$ are independently C$_1$-C$_6$alkyl groups or together part of cycloalkyl group and n is 1 or 2; —NH—R$^c$—NH—CO—CH$_2$—O—; —O—R$^c$—O—CH$_2$—O—; or a group of the formula —O—R$^c$—O— where R$^c$ is alkylene, arylene or a cycloalkylene group.

6. The method of claim 5 wherein V is oxygen.

7. The method of claim 5 wherein V is a NH group.

8. The method of claim 5 wherein V is a group of the formula —O—(CR$^a$R$^b$)$_n$—O—.

9. The method of claim 5 wherein V is an oxygen atom; a NH group; a group of the formula —O—(CR$^a$R$^b$)$_n$—O— where R$^a$ and R$^b$ are independently C$_1$-C$_6$alkyl groups or together part of cycloalkyl group and n is 1 or 2; —NH—R$^c$—NH—CO—CH$_2$—O—; —O—R$^c$—O—CH$_2$—O—; or a group of the formula —O—R$^c$—O— where R$^c$ is alkylene, arylene or a cycloalkylene group.

10. The method of claim 5, wherein the polyethylene glycol has a molecular weight of 30 kDa.

11. The method of claim 5, wherein the polyethylene glycol has a molecular weight of 35 kDa.

12. A compound, according to claim 1, wherein R$^2$ is a methyl group.

13. A compound, according to claim 1, wherein R$^7$ is a group of formula —CH(CH$_3$)CH$_2$CH$_3$.

14. A compound, according to claim 1, wherein R$^8$ is a hydrogen atom or a group of formula —CH$_2$OC(=O)R$^{17}$, wherein R$^{17}$ is a C$_1$-C$_6$ alkyl or a C$_2$-C$_6$ alkenyl group.

15. A compound, according to claim 1, wherein R$^9$ is a group of formula —CH(CH$_3$)$_2$.

16. A compound, according to claim 1, wherein V is an oxygen atom, a NH group, or a group of the formula —O—(CR$^a$R$^b$)$_n$—O—, whereby R$^a$ and R$^b$ independently from each other are C$_1$-C$_6$ alkyl groups, or, together, are part of a cycloalkyl group and n is 1 or 2; —NH—R$^c$—NH—CO—CH$_2$—O—, —O—R$^c$—O—CO—CH2-O—, or a group of formula —O—R$^c$—O—, whereby R$^c$ is an alkylene, arylene, or a cycloalkylene group.

17. A compound, according to claim 1, wherein the compound of Formula (I) is Tubulysin A.

18. A compound, according to claim 1, wherein the polymer is a polyethylene glycol (PEG).

19. A compound, according to claim 1, wherein the polyethylene glycol has a molecular weight of more than 30 kDa to 100 kDa.

* * * * *